United States Patent
Hanzlicek et al.

(10) Patent No.: US 10,076,584 B2
(45) Date of Patent: Sep. 18, 2018

(54) LOW ODOR LATEX PAINT CAPABLE OF REDUCING INTERIOR ODORS

(75) Inventors: Jennifer L. Hanzlicek, Macedonia, OH (US); Christopher J. Fox, Wellington, OH (US); Jean M. Dukles, Fairview Park, OH (US); Robert A. Martuch, Parma, OH (US); Anne M. Andrews, Kent, OH (US); Stuart F. Bedford, Hudson, OH (US)

(73) Assignee: The Sherwin-Williams Company, Cleveland, OH (US)

( * ) Notice: Subject to any disclaimer, the term of this patent is extended or adjusted under 35 U.S.C. 154(b) by 1429 days.

(21) Appl. No.: 13/089,763

(22) Filed: Apr. 19, 2011

(65) Prior Publication Data

US 2014/0343189 A1 Nov. 20, 2014

Related U.S. Application Data

(63) Continuation of application No. 12/645,590, filed on Dec. 23, 2009, now abandoned, which is a continuation of application No. 11/695,646, filed on Apr. 3, 2007, now abandoned.

(60) Provisional application No. 60/789,077, filed on Apr. 4, 2006.

(51) Int. Cl.
| | |
|---|---|
| *B05D 3/02* | (2006.01) |
| *A61L 9/014* | (2006.01) |
| *A61L 2/18* | (2006.01) |
| *A61L 9/01* | (2006.01) |
| *A61L 9/012* | (2006.01) |
| *C09D 5/02* | (2006.01) |
| *C09D 7/61* | (2018.01) |
| *C09D 7/63* | (2018.01) |
| *C08K 3/26* | (2006.01) |
| *C08K 5/098* | (2006.01) |

(52) U.S. Cl.
CPC ............... *A61L 9/014* (2013.01); *A61L 2/18* (2013.01); *A61L 9/01* (2013.01); *A61L 9/012* (2013.01); *C09D 5/024* (2013.01); *C09D 7/61* (2018.01); *C09D 7/63* (2018.01); *C08K 3/26* (2013.01); *C08K 5/098* (2013.01); *Y10T 428/12986* (2015.01)

(58) Field of Classification Search
CPC ... A61L 2/18; A61L 9/012; A61L 9/01; A61L 9/014; C09D 5/024; C09D 7/1216; C09D 7/61; C09D 7/63; Y10T 428/12986; C08K 3/26; C08K 5/098
USPC ......................................................... 427/384
See application file for complete search history.

(56) References Cited

U.S. PATENT DOCUMENTS

| | | | | | |
|---|---|---|---|---|---|
| 5,411,990 | A | * | 5/1995 | Tsuji | A01N 37/52 |
| | | | | | 514/372 |
| 5,441,981 | A | * | 8/1995 | Oppong | A01N 35/04 |
| | | | | | 514/544 |
| 2002/0132861 | A1 | * | 9/2002 | Uchiyama et al. | 516/198 |

FOREIGN PATENT DOCUMENTS

| | | | | |
|---|---|---|---|---|
| DE | 3808114 A1 | * | 9/1989 | A61K 8/27 |

OTHER PUBLICATIONS http://www.alternative-doctor.com/allergydotcom/chemicalcleanup.htm autho: Keith Scott-Mumby, accessed Jan. 11, 2009, copyrighted 2002.*
English translation of the abstract for DE 3808114.*

* cited by examiner

*Primary Examiner* — Robert S Walters, Jr.

(57) ABSTRACT

A paint composition, which in some embodiments, has a low odor in the container, while during after application to a surface, and once the paint has dried on a surface is disclosed. A method of making such a paint composition is disclosed. A paint composition and method are also disclosed which include using a paint to control certain odors in interior rooms.

12 Claims, No Drawings

LOW ODOR LATEX PAINT CAPABLE OF REDUCING INTERIOR ODORS

CROSS REFERENCE TO RELATED APPLICATIONS

This application is a Continuation of co-pending application Ser. No. 12/645,590 filed Dec. 23, 2009, which is a Continuation of application Ser. No. 11/695,646 filed Apr. 3, 2007, now abandoned, which claims priority from U.S. Provisional Application No. 60/789,077 filed on Apr. 4, 2006, the entirety of all of which are hereby incorporated by reference.

BACKGROUND

Latex paint and coating compositions are commonly used for providing protective or decorative coatings to walls or other surfaces. Latex paint compositions usually comprise water, a dispersed polymeric binder, and one or more pigments. The binder may be selected from various known polymeric binders such as vinyl, acrylic or urethane polymers.

Various odors are associated with latex paints. These odors may arise from components of the paint composition, such as buffers, solvents, biocides, thickening agents, or crosslinking agents. In some cases, during manufacture of a paint, some of the binder may decompose forming by-products such as acetates, short chain aldehydes, ketones, and fatty acids. Any of these components or other components can cause the paint to have an undesirable odor.

Latex paints are often used to paint interior surfaces, such as walls of residential and commercial buildings. Unpleasant odors, including but not limited to various cooking odors, cigarette smoke, pet odors, or mold or mildew odors etc. are often present in various environments. Generally, such odors are reduced by using agents such as air fresheners, scented candles, air purifiers, ionizers, ozonizers, and electrostatic filters, or other known agents or apparatus known to remove unpleasant odors from the air. However, these means for reducing or masking odors work only temporarily, need to be monitored or maintained, are not always available, and may have harmful or dangerous side effects. Thus, a continuous, passive, and unobtrusive means for reducing odors would be helpful.

DETAILED DESCRIPTION OF THE INVENTION

The present invention relates to a latex paint, which, in some embodiments, has a low odor whether in the container, while drying after application to a surface, and once the paint has dried on a surface. In addition, in some embodiments, a latex paint of the present invention, when applied to an interior surface, is capable of reducing odors in the area in which it is applied.

The present invention comprises a latex paint composition to which odor absorbing or adsorbing material may be added. Such odor absorbing or adsorbing materials may also be referred to herein as "entrapping agents." Odor absorbing materials include but are not limited to zeolites, cyclodextrins, and activated carbon. These materials are typically porous, such that an odor particle may associate with pores in the odor absorbing material to become trapped within the pore, thus removing the odor from the air. Odor adsorbing materials include activated carbon, sodium bicarbonate, and cyclodextrins. Odor particles chemically or physically associate with the surface of the odor adsorbing materials. Such association normally chemically or physically alters both the odor and the surface of the odor adsorbing material to remove the odor. In some cases, such chemical alteration sacrifices some of the surface activity of the adsorbing material. The present invention may also optionally comprise an odor neutralizing agent. Exemplary useful odor neutralizing agents include sodium bicarbonate, undecylenic acid, salts of undecylenic acid, and esters of undecylenic acid, undecylenate silicone esters, chloramine-T (n-chloro-para-toluene sulfonamide sodium salt), zinc ricinoleate, and combinations thereof. The latex paint of the present invention may also comprise a fragrance emitting compound or a re-odorant. Examples of fragrance emitting compounds or re-odorants include, but are not limited to cinnamaldehyde, citronella, eugenol, and vanilla extract or other natural extracts. Various other fragrances are commercially available from suppliers such as Shaw Mudge, Arylessence, or JE Sozio. In some cases, fragrances may be mixed with an odor neutralizing compound as described herein. In embodiments that include a fragrance compound, the fragrance may emit a pleasant scent while the other components of the paint reduce or neutralize malodors. Other materials such as nano-titanium dioxide or zinc oxide or anatase titanium dioxide, which are capable of degrading odors in the presence of an initiator, such as light, may also be used in some embodiments. Further, dry film preservatives, such as fungicides, biocides, or algaecides can be added as an odor preventative for certain environments that tend to have higher amounts of mold or mildew growth.

The odor reducing materials listed above or a fragrance may be post-added to an existing latex paint formulation. In one embodiment, one or more of these materials may be incorporated into a latex paint composition during the manufacture of the latex paint as will be described in more detail herein.

One type of odor absorbing or adsorbing material that may be useful in the present invention is a zeolite. One useful type of zeolite are the "intermediate" silicate/aluminate zeolites. The intermediate zeolites are characterized by $SiO_2/AlO_2$ molar ratios of less than about 10. In one useful embodiment, the molar ratio of $SiO_2/AlO_2$ ranges from about 2 to about 10. The intermediate zeolites may have an advantage over the "high" zeolites in that they have a higher affinity for odors, they are more weight efficient for odor adsorption because they have a larger surface area, and they are more moisture tolerant and retain more of their odor absorbing capacity in water than the high zeolites. However, it is contemplated that high zeolites may be used in the present invention as well. One example of a useful zeolite is crystalline aluminum silicate. A variety of zeolites suitable for use herein are commercially available and include VALFOR® CP301-68, VALFOR® CP300-63, VALFOR® CP300-35, and VALFOR® CP300-56 available from PQ Corporation; zeolites marketed under the trademarks ABSCENTS and SMELLRITE by Union Carbide Corporation and UOP; and SYLOSIV K300 or SYLOSIV A3 from Grace Davison. Zeolites used in the present invention may be in the form of a powder having a particle size that is for example, less than about 40 microns, further for example, less than about 20 microns, even further for example, less than about 10 microns, and finally for example, about 3 to about 5 microns.

Zeolites may be included in paint formulations of the present invention in amounts up to about 10% by weight of a total paint formulation. For example, a zeolite may comprise about 2% to about 5% by weight of a total paint formulation, for example about 2.5% to about 3%.

Another type of odor adsorbing or absorbing material that may be useful are cyclodextrins. The "cyclodextrin" may be any of the known cyclodextrins such as unsubstituted cyclodextrins containing from six to twelve glucose units, especially alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in donut-shaped rings. The specific coupling and conformation of the glucose units give the cyclodextrins a rigid, conical molecular structure with hollow interiors of specific volumes. The "lining" of each internal cavity is formed by hydrogen atoms and glycosidic bridging oxygen atoms; therefore, this surface is fairly hydrophobic. The shape and physical-chemical properties of the cavity enable the cyclodextrin molecules to absorb (form inclusion complexes with) organic molecules or parts of organic molecules which can fit into the cavity, especially the malodor molecules which exist in latex paints and other aqueous coatings. Therefore, cyclodextrins, and especially mixtures of cyclodextrins with different size cavities, can be used to complex with the unwanted odor molecules. The complexation between cyclodextrin and the malodorous molecules occurs particularly rapidly in the presence of water. However, the extent of the complex formation can also depend on the polarity of the absorbed malodor molecules. Other cyclodextrins can be specifically designed and tailored to specific malodors and can be used in this manner as well.

In one embodiment, the cyclodextrins contemplated for use in the present invention are highly water-soluble, such as alpha-cyclodextrin and/or derivatives thereof, gamma-cyclodextrin and/or derivatives thereof, derivatized beta-cyclodextrins, and/or mixtures thereof. The derivatives of cyclodextrin consist mainly of molecules wherein some of the OH groups are converted to OR groups. Cyclodextrin derivatives include, for instance, those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a —$CH_2$—$CH(OH)$—$CH_3$ or a —$CH_2CH_2$—OH group; branched cyclodextrins such as maltose-bonded cyclodextrins; cyclodextrin glycerol ethers with structure analogous to hydroxypropyl cyclodextrins, but with the side chains forming —$CH_2CH(CH_2OH)$— bridges between 2' and 3' hydroxyl oxygens on the glucosyl units; cationic cyclodextrins such as those containing 2-hydroxy-3-(dimethylamino)propyl ether, wherein R is $CH_2$—$CH(OH)$—$CH_2$—$(CH_3)_2$ which is cationic at low pH; quaternary ammonium, e.g., 2-hydroxy-3-(trimethyl-ammonio) propyl ether chloride groups, wherein R is $CH_2$—$CH(OH)$—$CH_2$—$N+(CH_3)_3Cl$—; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3,6-anhydrocyclodextrins, and mixtures thereof. Other cyclodextrin derivatives are disclosed in U.S. Patent Application Publication No. 2002-0132861 and the references cited therein.

Highly water-soluble cyclodextrins are those having water solubility of at least about 10 g in 100 ml of water at room temperature, for example, at least about 20 g in 100 ml of water, and further for example, at least about 25 g in 100 ml of water at room temperature.

Examples of water-soluble cyclodextrin derivatives suitable for use herein are hydroxypropyl alpha-cyclodextrin, methylated alpha-cyclodextrin, methylated beta-cyclodextrin, hydroxyethyl beta-cyclodextrin, hydroxypropyl beta-cyclodextrin, hydroxypropyl gamma-cyclodextrin, and methylated gamma-cyclodextrin. Hydroxyalkyl cyclodextrin derivatives preferably have a degree of substitution of from about 1 to about 14, for instance, from about 1.5 to about 7, wherein the total number of OR groups per cyclodextrin is defined as the degree of substitution. Methylated cyclodextrin derivatives typically have a degree of substitution of from about 1 to about 18, preferably from about 3 to about 16. A known methylated beta-cyclodextrin is heptakis-2,6-di-O-methyl-beta-cyclodextrin, commonly known as DIMEB, in which each glucose unit has about 2 methyl groups with a degree of substitution of about 14. One useful, commercially available, methylated beta-cyclodextrin is a randomly methylated beta-cyclodextrin, commonly known as RAMEB, having different degrees of substitution. Such cyclodextrins are commercially available, for instance, from Cerestar USA, Inc. and Wacker Chemicals (USA), Inc.

Additional useful cyclodextrins include cyclohexylamylose, cycloheptylamylose, and cyclooctaamylose available as CAVAMAX W-6, W-7, and W-8 respectively from Wacker Chemicals, Inc.

In one embodiment, a mixture of cyclodextrins may be used. Such mixtures may absorb odors more broadly by complexing with a wider range of odoriferous molecules having a wider range of molecular sizes. At least a portion of the cyclodextrins may be alpha-cyclodextrin and derivatives thereof, gamma-cyclodextrin and derivatives thereof, and/or derivatized beta-cyclodextrin; for example, a mixture of alpha-cyclodextrin, or an alpha-cyclodextrin derivative, and derivatised beta-cyclodextrin, further for example, a mixture of derivatised alpha-cyclodextrin and derivatised beta-cyclodextrin; and finally for example, a mixture of hydroxypropyl alpha-cyclodextrin and hydroxypropyl beta-cyclodextrin, and/or a mixture of methylated alpha-cyclodextrin and methylated beta-cyclodextrin.

When used in paint formulations of the present invention, a cyclodextrin or mixtures of cyclodextrins may comprise up to about 10% by weight of the paint. In one useful embodiment, a cyclodextrin or mixtures of cyclodextrins may comprise about 1% to about 3%, for example, about 1.5 to about 2% by weight of the paint formulation.

In one embodiment of the present invention, the entrapping agent, such as cyclodextrin, is used in uncomplexed form. The same may apply to other entrapping agents used in the invention. That is, they are added in a form such that they are capable of forming complexes with the odor molecules present in the latex-based coating material to be treated.

In another useful embodiment of the present invention, activated carbon may be used as an odor absorbing or adsorbing material. Carbon materials that may be suitable for use in the present invention include, but are not limited to those materials known commercially as absorbents for organic molecules or for air purification purposes. Various types of activated carbon are commercially available from companies such as Calgon Carbon Corporation, or LQ-325 available from Carbochem, Inc. In one useful embodiment, activated carbon particles used in the present invention have a particle size of about 40 microns or less. When used as an odor entrapping agent in the present invention, activated carbon may be included in paints in amounts up to about 5% by weight of the total paint, for example, about 2% to about 3% by weight.

Another useful odor neutralizing/entrapping agent is sodium bicarbonate. Although commercial grades of sodium bicarbonate may be used in the present invention, in some embodiments of the invention, finer grades of sodium bicarbonate may be particularly useful, especially when larger amounts of sodium bicarbonate are included in the paint formulation. The use of such smaller solid particles may result in a more attractive appearance of the dried paint film. For example, in one embodiment, the sodium bicarbonate particles may be the same size as typical extender pigment particles used in latex paint formulations. As another example, the sodium bicarbonate particles may have a maximum particle size of about 90 microns or less, for example the maximum particle size may be about 70 microns, about 60, microns, about 50 microns, about 40 microns, about 35 microns, about 30 microns, about 25 microns, about 20 microns, about 15 microns, or about 10 microns. In some embodiments, the particle size of the sodium bicarbonate may be measured by the mean particle size. The mean particle size may be for example, about 90 microns, about 70 microns, about 60 microns, about 50 microns, about 40 microns, about 35 microns, about 30 microns, about 25 microns, about 20 microns, about 15 microns, about 10 microns, or about 5 microns.

In one useful embodiment of the present invention, sodium bicarbonate may be added up to the maximum amount wherein the paint will remain a stable dispersion for application. In another embodiment, sodium bicarbonate may be added up to the maximum amount wherein the paint will remain a stable dispersion for application with some solid sodium bicarbonate dispersed in the paint. In another embodiment, sodium bicarbonate may be added in a sufficient amount for at least some solid sodium bicarbonate to be dispersed in the paint such that the sodium bicarbonate may be redispersed if settling occurs during storage. In other embodiments, the sodium bicarbonate may be dissolved in the paint composition. For example, in some paints, sodium bicarbonate may be added in amounts up to about 40% by weight of the total paint composition. In an alternative embodiment, the sodium bicarbonate may comprise about 0.25% to about 33% by weight of the paint composition. Further for example, the sodium bicarbonate may comprise at least 3.2% by weight of the paint formulation, for example, about 5% to about 10% by weight of the paint composition. Even further for example, the sodium bicarbonate may comprise about 7% to about 9% by weight of the paint composition.

In another embodiment, the amount of sodium bicarbonate added to a paint may be calculated based on the amount of sodium bicarbonate in the paint film when dried. In one useful embodiment, sodium bicarbonate may comprise about 0.5% to about 17.3% of a dry paint film.

In one useful embodiment of the present invention, an agent may be added to a paint composition to raise the pH of the paint to lower the solubility of sodium bicarbonate in the paint composition. Such a pH increasing agent may allow additional loading of sodium bicarbonate into a paint composition to increase the free solid sodium bicarbonate in the paint. In one useful embodiment, a paint composition containing sodium bicarbonate may be made wherein the pH of the paint composition is about 9.2.

Paints containing sodium bicarbonate as described herein may also be useful for preventing rust formation on metal surfaces to which the paint is applied. Paints containing about 0.5 to about 8%, for example, about 1%, about 2%, and about 4%, by weight sodium bicarbonate have been observed to reduce or eliminate the formation of rust or flash rusting. In addition, paint containing sodium bicarbonate as described herein may be able to inhibit the growth of bacteria in containers of paint and on surfaces to which paint is applied. The inhibition of bacterial, mold or fungal growth was observed with the use of sodium bicarbonate alone or in combination with other dry film preservatives as described herein.

Odor neutralizing agents may also be added to latex paints of the present invention. One useful type of odor neutralizing agent is disclosed in U.S. Pat. No. 6,495,097. This patent discloses undecylenic acid, salts of undecylenic acid (e.g. sodium, calcium, and zinc), simple esters of undecylenic acid (e.g. methyl, ethyl, propyl, and butyl), undecylenate silicone esters, and combinations of undecylenic acid esters as odor neutralizing agents.

The various odor entrapping/neutralizing agents described above may be added to paint alone or in various combinations. Useful combinations include, but are not limited to, sodium bicarbonate and undecylenic acid, salts of undeceylenic acid, or esters of undecylenic acid; sodium bicarbonate and zeolite; sodium bicarboate, zeolite and cyclodextrin; and zeolite and cyclodextrin. The combinations of entrapping/neutralizing agents may be added in amounts up to about 20% by weight of the paint composition, for example up to about 10% by weight, further for example up to about 5% by weight. It is contemplated that formulations containing these odor entrapping/neutralizing agents will be capable of reducing the odor emitted by the paint itself both prior to application as well as in the applied paint and in the dried paint film. It is also contemplated that paints containing the odor entrapping/neutralizing agents as described herein will be capable of reducing odors in an interior room where the paint is applied.

Dry film preservatives, such as biocides or fungicides, may also be added to paints to prevent odors. Chemicals used as biocides or fungicides include, but are not limited to carbendazim, chlorothalonil, 3-iodo-2-propynyl butyl carbamate (IPBC), 1,2-benzisothaiazolin-3-one (BIT), sodium omadine, zinc omadine, zinc oxide, tetrahydro-3,5-dimethyl-2H-1, 3,5-thiadiazine-2-thione solution, 5-hydroxymethoxymethyl-1-AZA-3, 7-dioxabicyclo[3.3.0] octane formaldehyde release type preservative, 2-n-octyl-4-isothiazolin-3-one, 1-(3-chloroallyl)-3,5,7-triaza-1-azoniaadamantane chloride. Various such biocides or fungicides are commercially available such as Mergal BCM from Troy Chemical Company, Nuocide 960 from ISP Technologies, Inc., Arch Zinc Omadine and Proxel GXL from Arch Chemicals. Depending on the activity of a particular biocide or fungicide (either solid or in solution), the biocide may comprise about 0.05% to about 1.2% by weight of the total paint formulation.

Paint compositions in which the odor entrapping or neutralizing agents may be useful generally contain from about 2% to about 65% by weight binder, for example, about 15% to about 25%. Binders useful in latex paint compositions are known in the art and include polymeric binders, such as acrylics, or non-polymeric binders. The water content may be from about 30% to about 95%, for instance from about 40% to about 65%. The composition may also include thickeners, such as urethane thickeners, hydroxyethyl cellulose thickeners, and acrylic thickeners in amounts up to about 10% by weight, for example about 1% to about 2%. The content of inorganic materials may be from about 5% to about 50% by weight, for example, about 10% to about 40%.

Such inorganic components may comprise titanium dioxide (e.g. 0 to about 30% titanium dioxide) based on the nature of the coating compositions. Other colored pigments may also be used alone or in combination to produce a wide range of colored paint. Suitable additional pigments may include calcium carbonate, talc, clay, silicates, aluminum silicates, calcium metasilicates, aluminum potassium silicates, magnesium silicates, barium sulfates, nepheline syenite, feldspar, zinc oxides or sulfides, or others known to those skilled in the art. Such pigments may be included in amounts up to about 60% by weight, for example, about 10% to about 20%. Synthetic organic materials might also be incorporated; these include plastic beads, hollow spheres or other similar materials. Other optional components include glycols such as ethylene and/or propylene glycol in amounts from 0 to about 7% and other solvents such as diethylene glycol dibenzoate and dipropylene glycol dibenzoate in amounts up to about 3%. The coating composition may also contain pigment dispersing agents which can be solvents or surfactants; biocides such as amine or sulfur compounds, halogen donors, or metals; foam control agents such as oils, fatty acids and silicones; slip and mar additives; adhesion promoters, and/or other known paint additives.

In use in latex paint formulations, the solid odor entrapping or neutralizing agents, such as sodium bicarbonate, cyclodextrins, zeolites, and activated carbon may be added to an existing paint, either in solid form, or in a slurry with water or other appropriate carrier liquid. In another embodiment, such solid odor entrapping agents may be incorporated into the pigment grind paste used to manufacture the paint. Methods for making pigment grind pastes are well known in the art. In still another embodiment, some quantity of the odor entrapping/neutralizing agent or agents may be added during manufacture (such as to the grind paste) while another quantity may be post-added to the finished paint. In one useful embodiment, adjustments may be made to the remainder of the paint formulation to accommodate for the additional solid materials incorporated into the grind paste. Such modifications would be understood by those skilled in the art. Both post adding such odor reducing materials or adding such odor reducing materials to the grind paste, in some embodiments, may reduce the odor emitted prior to application of the coating to the substrate as well as odors emitted as the coating dries after application and after the coating, and odors emitted after the coating has dried.

In order to control odors in an interior room, the odor entrapping or neutralizing agents, such as sodium bicarbonate, zeolites, cyclodextrin, activated carbon, and undecylenic acid and its derivatives, may be added to a paint composition, alone or in various combinations, either during or after the manufacture of the paint. The paint may be applied to one or more walls of an interior room where it is desired to reduce odors on a continuous basis. In some embodiments of the invention, after such paint has dried, it is contemplated that the paint composition will reduce odors introduced into the room on a continuous basis for a period of time.

The present invention will be better understood by reference to the following examples, which are provided for purposes of illustration only and are not to be construed as limiting the scope of the present invention. As used in the example, unless otherwise noted, "Parts by Weight" means weight percent.

Example 1

A representative odor-reducing latex coating composition may be prepared by admixing the following ingredients:

| Raw Material | Parts by Weight |
| --- | --- |
| Styrene Acrylic Latex[1] | 23.34 |
| Titanium Dioxide slurry | 20.42 |
| Water | 19.11 |
| Nepheline syenite | 11.25 |
| Sodium Bicarbonate | 8.00 |
| Calcium Carbonate | 4.62 |
| Aluminum Silicate slurry[2] | 4.04 |
| Aluminum potassium silicate | 2.31 |
| 25% Sodium Hydroxide Solution | 1.75 |
| Calcined clay | 1.44 |
| Thickener[3] | 1.00 |
| Mineral Oil Defoamer[4] | 0.60 |
| Plasticizer[5] | 0.60 |
| Thickener[6] | 0.33 |
| Tetra-potassium pyrophosphate | 0.28 |
| Nonionic surfactant[7] | 0.27 |
| Surfactant[8] | 0.27 |
| Zinc omadine 45% solution | 0.21 |
| Benzisothiazolone biocide | 0.15 |

In this example, the sodium bicarbonate may be incorporated into the grind paste during the manufacture of the paint.
[1] A proprietary styrene acrylic latex of the assignee of this application.
[2] Such slurries are commercially available and generally comprise various combinations of dry pigment and one or more of: dispersant and/or surfactant, buffer, biocide, water, and/or defoamers.
[3] ACRYSOL SCT-275 from Rohm & Haas.
[4] SHERDEFOAM #2 - a proprietary defoamer of the assignee of this application.
[5] BENZOFLEX B-50 plasticizer from Velsicol Chemical.
[6] ACRYSOL TT-935 from Rohm & Haas.
[7] TRITON N-57 nonionic surfactant from Dow Chemical.
[8] DEXTROL OC-50 anionic surfactant from Dexter Chemical LLC Example 2

A representative odor reducing latex coating composition may be prepared by admixing the following ingredients:

| Raw Material | Parts by Weight |
| --- | --- |
| Latex of Example 1 | 23.5 |
| Water | 21.5 |
| Titanium Dioxide slurry | 20.6 |
| Nepheline syenite | 13.6 |
| Calcium Carbonate | 5.6 |
| Aluminum Silicate slurry | 4.8 |
| Aluminum potassium silicate | 2.6 |
| Zeolite | 2.5 |
| Calcined clay | 1.8 |
| SHERDEFOAM #2 | 0.6 |
| BENZOFLEX B-50 | 0.6 |
| ACRYSOL SCT-275 | 0.4 |
| ACRYSOL TT-935 | 0.4 |
| 25% Sodium Hydroxide Solution | 0.3 |
| Tetra-potassium pyrophosphate | 0.3 |
| TRITON N-57 surfactant | 0.3 |
| DEXTROL OC-50 surfactant | 0.3 |
| Zinc omadine 48% solution | 0.2 |
| Benzisothiazolone biocide | 0.2 |

In this example, the zeolite may be incorporated into the grind paste during the manufacture of the paint.

Example 3

A representative odor reducing latex coating composition may be prepared by admixing the following ingredients:

| Raw Material | Parts by Weight |
| --- | --- |
| Latex of Example 1 | 23.5 |
| Water | 21.5 |
| Titanium Dioxide slurry | 20.6 |

-continued

| Raw Material | Parts by Weight |
| --- | --- |
| Nepheline syenite | 13.6 |
| Calcium Carbonate | 5.6 |
| Aluminum Silicate slurry | 4.8 |
| Aluminum potassium silicate | 2.6 |
| Cyclodextrin | 2.5 |
| Calcined clay | 1.8 |
| SHERDEFOAM #2 | 0.6 |
| BENZOFLEX B-50 | 0.6 |
| ACRYSOL SCT-275 | 0.4 |
| ACRYSOL TT-935 | 0.4 |
| 25% Sodium Hydroxide Solution | 0.3 |
| Tetra-potassium pyrophosphate | 0.3 |
| TRITON N-57 surfactant | 0.3 |
| DEXTROL OC-50 surfactant | 0.3 |
| Zinc omadine 48% solution | 0.2 |
| Benzisothiazolone biocide | 0.2 |

In this example, the cyclodextrin may be incorporated into the grind paste during the manufacture of the paint.

Example 4

A representative odor reducing latex coating composition may be prepared by admixing the following ingredients:

| Raw Material | Parts by Weight |
| --- | --- |
| Latex of Example 1 | 23.6 |
| Water | 21.7 |
| Titanium Dioxide slurry | 20.6 |
| Nepheline syenite | 12.1 |
| Calcium Carbonate | 4.9 |
| Aluminum Silicate slurry | 4.2 |
| Aluminum potassium silicate | 2.6 |
| Zeolite | 2.5 |
| Cyclodextrin | 2.5 |
| Calcined clay | 1.6 |
| SHERDEFOAM #2 | 0.6 |
| BENZOFLEX B-50 | 0.6 |
| ACRYSOL SCT-275 | 0.4 |
| ACRYSOL TT-935 | 0.4 |
| 25% Sodium Hydroxide Solution | 0.3 |
| Tetra-potassium pyrophosphate | 0.3 |
| TRITON N-57 surfactant | 0.3 |
| DEXTROL OC-50 surfactant | 0.3 |
| Zinc omadine 48% solution | 0.2 |
| Benzisothiazolone biocide | 0.2 |

In this example, the zeolite and cyclodextrin may be incorporated into the grind paste during the manufacture of the paint.

Example 5

A representative odor reducing latex coating composition may be prepared by admixing the following ingredients:

| Raw Material | Parts by Weight |
| --- | --- |
| Titanium Dioxide slurry | 23.7 |
| Vinyl Acrylic Latex[1] | 23.2 |
| Water | 17.3 |
| Calcite | 15.2 |
| Opaque Polymer[2] | 6.3 |
| Aluminum Silicate Slurry | 5.9 |
| Zeolite | 2.4 |
| Cyclodextrin | 1.4 |
| Butyl Carbitol | 0.8 |
| Dispersant[3] | 0.8 |
| Defoamer[4] | 0.6 |
| BENZOFLEX B-50 | 0.6 |
| Hydrous Magnesium Aluminum Silicate | 0.4 |
| Urethane Thickener[5] | 0.3 |
| ACRYSOL SCT-275 | 0.3 |
| Nonionic surfactant[6] | 0.3 |
| Zinc omadine 48% solution | 0.3 |
| 2-amino-2-methyl-1-propanol (95%) | 0.1 |
| Cellulosic Thickener | 0.04 |
| Benzisothiazolone biocide | 0.02 |
| Yellow Colorant | 0.008 |
| Red Colorant | 0.005 |
| Blue Colorant | 0.002 |

[1] A variety of commercially available acrylic latexes may be used, for example, various vinyl acrylic latexes are available from the UCAR Emulsion Systems division of Dow Chemicals.
[2] ROPAQUE OP-96 from Rohm & Haas.
[3] TAMOL 731A from Rohm & Haas.
[4] SHERDEFOAM #1, a proprietary defoamer of the assignee of the present application.
[5] ACRYSOL RM-2020 from Rohm & Haas.
[6] TRITON X-102 from Dow.

Example 6

A representative odor reducing latex coating composition may be prepared by admixing the following ingredients:

| Raw Material | Parts by Weight |
| --- | --- |
| Calcium Carbonate | 27.3 |
| Vinyl Acrylic Latex of Example 5 | 23.4 |
| Titanium Dioxide slurry | 23.4 |
| Water | 14.4 |
| Zeolite | 3.0 |
| Opaque Polymer[2] | 1.9 |
| Cyclodextrin | 1.7 |
| Butyl Carbitol | 0.8 |
| TAMOL 731A | 0.8 |
| ACRYSOL RM-2020 | 0.8 |
| SHERDEFOAM #1 | 0.6 |
| ACRYSOL SCT-275 | 0.5 |
| BENZOFLEX B-50 | 0.3 |
| Sodium Bicarbonate | 0.3 |
| Hydrous Magnesium Aluminum Silicate | 0.2 |
| 2-amino-2-methyl-1-propanol (95%) | 0.2 |
| TRITON X-102 surfactant | 0.2 |
| Zinc omadine 48% solution | 0.2 |
| Benzisothiazolone biocide | 0.02 |

In this example, the cyclodextrin, zeolite and sodium bicarbonate may be incorporated into the grind paste during the manufacture of the paint.

Example 7

A representative odor reducing latex coating composition may also be prepared by mixing 30 parts by weight sodium bicarbonate into a paint made according to Example 4.

Example 8

Sodium bicarbonate, zeolite, cyclodextrin, and activated carbon were each added to separate batches of commercial paint compositions, SUPERPAINT® exterior satin and DURATION HOME® interior satin paint, available from the assignee of the present application. The sodium bicarbonate was post-added to finished paint compositions in an amount of 8% by weight of the total paint. The zeolite, cyclodextrin, and activated carbon were each post-added added in amounts of 2% by weight of the total paint.

Individuals were asked to evaluate the smell of the same paint with and without the odor reducing agents. For these two paints, it was observed that the paints having the odor reducing agent added had less odor than the paint without the odor reducing agent added.

While the present invention has been illustrated by the description of embodiments thereof, and while the embodiments have been described in considerable detail, it is not the intention of the applicants to restrict or in any way limit the scope of the appended claims to such detail. For example, although the invention has been described with reference to latex paints, it is contemplated that the concepts herein may also be applicable to other types of paints that are known in the art. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicant's general inventive concept.

What is claimed is:

1. A paint composition comprising:
    a latex binder;
    water;
    an odor entrapping agent selected from the group consisting of cyclodextrin, zeolite, and activated carbon; and
    at least one odor neutralizing agent selected from the group consisting of undecylenic acid, salts of undecylenic acid, esters of undecylenic acid, undecylenate silicone esters, n-chloro-para-toluene sulfonamide sodium salt, and zinc ricinoleate;
    wherein said paint, when dry, removes odors from an interior room.

2. The paint composition of claim 1 wherein the at least one odor neutralizing agent is selected from the group consisting of undecylenic acid, salts of undecylenic acid, esters of undecylenic acid, and undecylenate silicone esters.

3. The paint composition of claim 1 wherein the at least one odor neutralizing agent is n-chloro-para-toluene sulfonamide sodium salt.

4. The paint composition of claim 1 wherein the at least one odor neutralizing agent is zinc ricinoleate.

5. A process for reducing odors in an interior room comprising:
    applying a latex-based paint to one or more walls of said interior room, said paint comprising: a binder, water, an odor entrapping agent selected from the group consisting of cyclodextrin, zeolite, and activated carbon; and at least one odor neutralizing agent selected from the group consisting of undecylenic acid, salts of undecylenic acid, esters of undecylenic acid, undecylenate silicone esters, n-chloro-para-toluene sulfonamide sodium salt, and zinc ricinoleate; and
    allowing said paint to dry.

6. The process of claim 5 wherein the at least one odor neutralizing agent is selected from the group consisting of undecylenic acid, salts of undecylenic acid, esters of undecylenic acid, and undecylenate silicone esters.

7. The process of claim 5 wherein the at least one odor neutralizing agent is n-chloro-para-toluene sulfonamide sodium salt.

8. The process of claim 5 wherein the at least one odor neutralizing agent is zinc ricinoleate.

9. A dry paint film comprising:
    a binder;
    an odor entrapping agent selected from the group consisting of cyclodextrin, zeolite, and activated carbon; and
    at least one odor neutralizing agent selected from the group consisting of undecylenic acid, salts of undecylenic acid, esters of undecylenic acid, undecylenate silicone esters, chloramine-T (n-chloro-para-toluene sulfonamide sodium salt), and zinc ricinoleate.

10. The dry paint film of claim 9 wherein the at least one odor neutralizing agent is selected from the group consisting of undecylenic acid, salts of undecylenic acid, esters of undecylenic acid, and undecylenate silicone esters.

11. The dry paint film of claim 9 wherein the at least one odor neutralizing agent is n-chloro-para-toluene sulfonamide sodium salt.

12. The dry paint film of claim 9 wherein the at least one odor neutralizing agent is zinc ricinoleate.

* * * * *